(12) United States Patent
Daigle

(10) Patent No.: US 7,207,242 B1
(45) Date of Patent: Apr. 24, 2007

(54) UNIVERSAL ROTARY DEVICE FOR MARKING AN ARTICLE WITH INK

(76) Inventor: Ronald Daigle, 20 Nickerson St., Cranston, RI (US) 02910

( * ) Notice: Subject to any disclaimer, the term of this patent is extended or adjusted under 35 U.S.C. 154(b) by 0 days.

(21) Appl. No.: 11/219,370

(22) Filed: Sep. 2, 2005

Related U.S. Application Data

(60) Provisional application No. 60/608,477, filed on Sep. 10, 2004.

(51) Int. Cl.
*B43K 5/00* (2006.01)
(52) U.S. Cl. ............... 81/9.22; 30/362; 606/186
(58) Field of Classification Search ........... 81/9.22; 30/362; 606/185, 186
See application file for complete search history.

(56) References Cited

U.S. PATENT DOCUMENTS

| | | | | |
|---|---|---|---|---|
| 4,159,659 A * | 7/1979 | Nightingale | ............ | 81/9.22 |
| 4,782,725 A * | 11/1988 | Spaulding | ............ | 81/9.22 |
| 4,914,988 A * | 4/1990 | Chang | ............ | 81/9.22 |
| 5,279,552 A * | 1/1994 | Magnet | ............ | 81/9.22 |
| 5,551,319 A * | 9/1996 | Spaulding et al. | ............ | 81/9.22 |

* cited by examiner

*Primary Examiner*—Hadi Shakeri

(57) ABSTRACT

A marking device with a reciprocating needle is disclosed. The needle is attached to a drive mechanism that is linearly reciprocated via a drive motor. The needle is contained within a removable grip tube for adjustability of the exposed length of the needle end, the needle further including a stabilization mechanism limiting the movements of the needle to linear reciprocating motion. The device includes an open design for easy removal and replacement of device components and allows for utilization of varying dimensioned components such as tubes, needles, and motors available from a variety of manufacturers.

16 Claims, 3 Drawing Sheets

UNIVERSAL ROTARY DEVICE FOR MARKING AN ARTICLE WITH INK

CROSS REFERENCE TO RELATED APPLICATIONS

This application claims the benefit of U.S. Provisional Application No. 60/608,477 filed 10 Sep. 2004.

FIELD OF THE INVENTION

This invention relates to a reciprocating shaft device for marking of articles and for identification of the skin of animals or humans, and more specifically to a tattoo device including such a reciprocating shaft device.

BACKGROUND OF THE INVENTION

Devices in the field of the present invention are used to place ink below the surface of an object or article. A pin or needle punctures the surface and places the ink below the surface. When the surface of the skin is a living being, the ink is placed at such a level in the skin where it remains permanently. Because the ink is permanent, it is very important that the ink be applied very precisely. Correspondingly, it is very important that the position of the needle when it punctures the surface can be precisely controlled. The needle must be moved back and forth in a reciprocating motion in order to puncture the surface, and this motion must be very limited in a direction perpendicular to the reciprocating motion.

Devices having a reciprocating shaft and specifically tattoo devices are well known. Some existing units use an open, mechanical make-and-break electrical contact system, which drives an electromechanical operated pivot arm, which vibrates up and down. Other versions use electric motors with eccentric cams to drive an arm up and down. The make-and-break units have visible sparking contacts and produce a high degree of noise when in use. Because of the sparking, such tattoo units may not be used in operating rooms or other environments where flammable or explosive gasses are present. The make-and-break units also require constant adjustment due to changes in resiliency of the contact spring. Rubber bands are required to hold the needle bars in place and reduce vibration.

The prior art designs utilize custom components that preclude users from utilizing parts and accessories already in possession or that are commercially available through different suppliers. With the instant invention, the "open" design allows for the device to utilize preexisting tubes, needles, components, etc, of different sizes and available from a variety of different manufacturers. Furthermore, the device can be maintained by someone without any specialized mechanical skills with all components and adjustments easily accessible for routine maintenance.

SUMMARY OF THE INVENTION

It is an object of the present invention to provide a marking device with reciprocating movement, and more specifically, a device which utilizes off the shelf components and is adaptable to utilize various needle and needle tube configurations.

A marking device according to the present invention utilizes an open framed design allowing easy access to all components for adjustment, maintenance and repair. The opened framed design exposes the operator to the operation of the machine and relationships between parts and components. This allows the operator to become quickly acclimated to its operation with little familiarization or training. Operation is intuitive and and acclimation to the device is rapid. The device is designed to utilize commercially available parts that are readily available from local supply stores, internet suppliers, and mail order catalog stores. Referring to FIG. 1, normal wear maintenance items include needles (26), tubes (27), and rotary drive motor (7). Repairs are easily performed by an operator with no special skills or training utilizing common tools. All components are easily accessible with repairs requiring only a few minutes to complete. Adjustments of the device are also easy to accomplish. Needle depth adjustments can be made by loosening the tightening screw 17 and varying the tube 27 position in the frame 10 then retightening tube 17 to lock the tube in position. Needle speed adjustment and operation are easily controlled by a commercially available variable 12 Volt power supply and interrupter switch.

BRIEF DESCRIPTION OF THE DRAWINGS

The invention is best understood from the following detailed description when read in connection with the accompanying drawings, which illustrate an embodiment of the present invention.

DETAILED DESCRIPTION OF THE INVENTION

Figure 1:
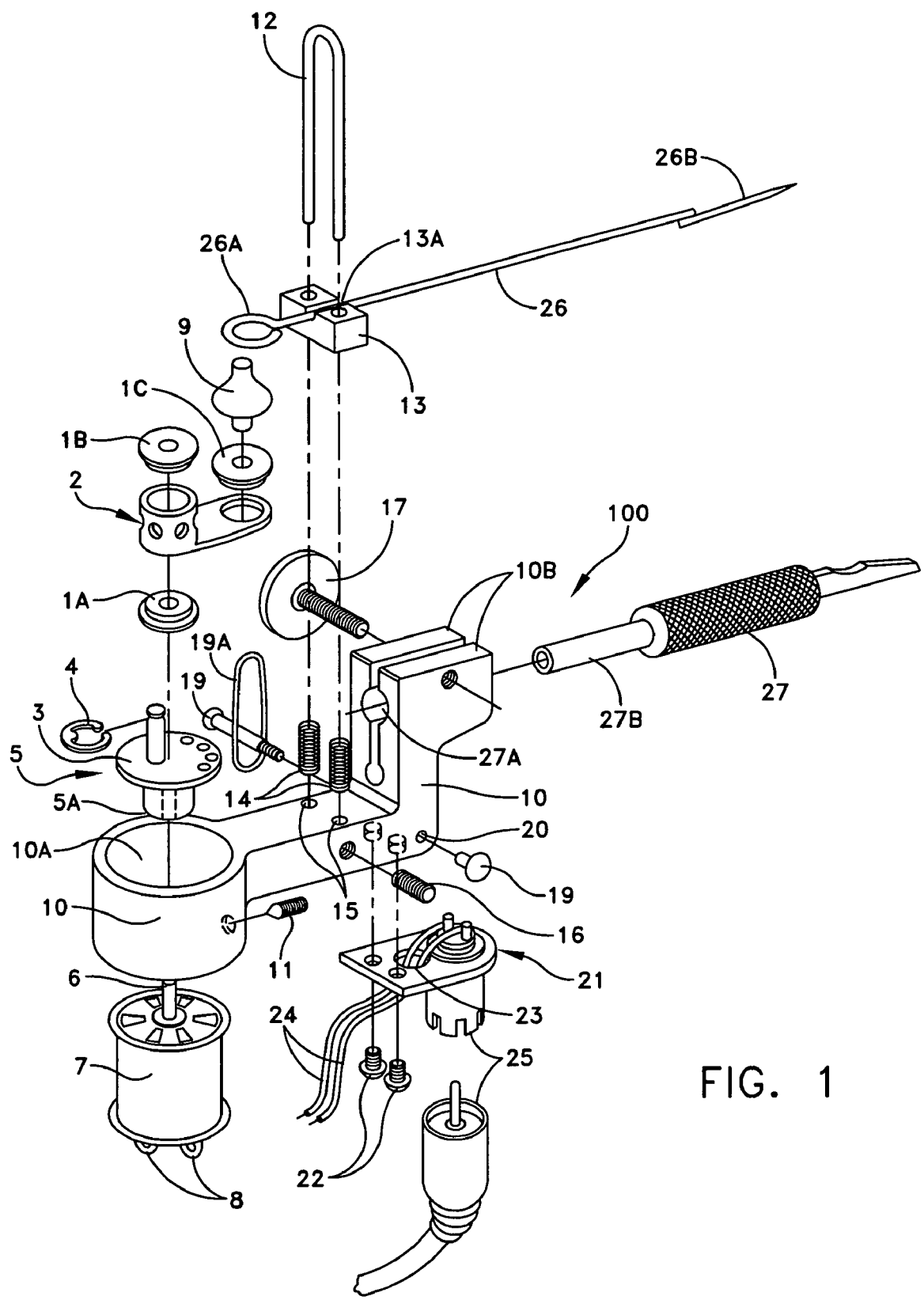
FIG. 1 illustrates an exploded view of a preferred embodiment of subject invention.
Figure 1A:
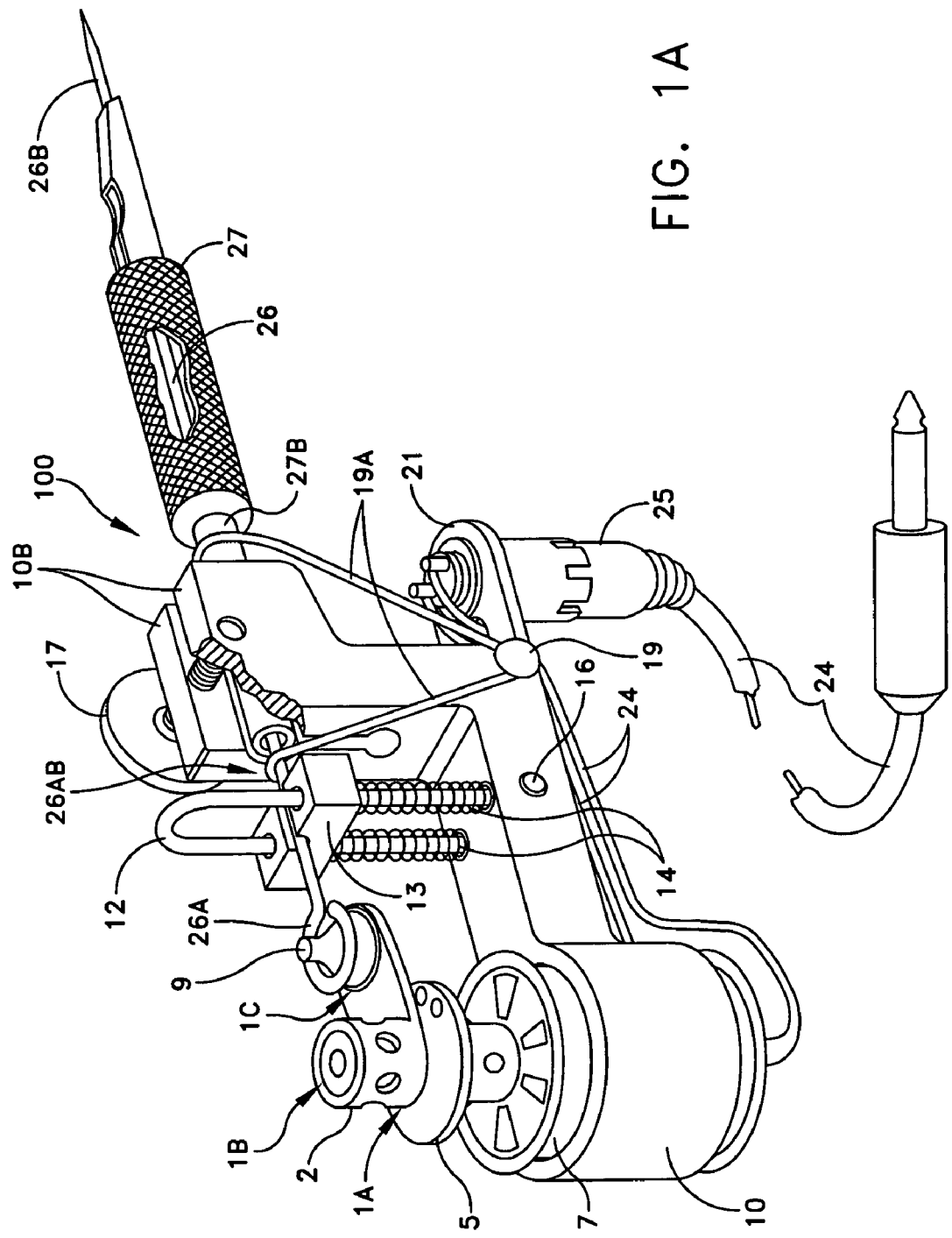
FIG. 1A illustrates the preferred embodiment of FIG. 1, showing subject invention in its assembled state, and further illustrating the guide mechanism in the tensioned state (ready for use) and the placement of elastic 19A.
Figure 1B:
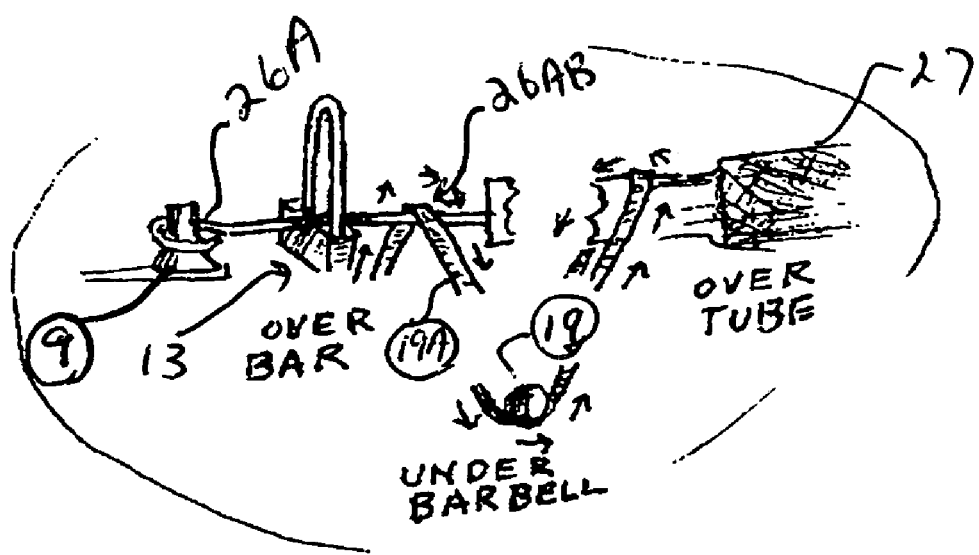
FIG. 1B illustrates a detailed view of the placement of elastic 19A in the preferred embodiment of FIG. 1A.

FIG. 1 illustrates an exploded view of the Universal Rotary Device 100 in its disassembled state. FIG. 1A illustrates a Universal Rotary Device 100 in its assembled state. Referring to FIGS. 1 and 1A, power to rotary device 100 is supplied through RCA jack 25 via a 12 volt power supply and interrupter switch (not shown). Bracket 21 houses female end of RCA Jack 25 and is secured to frame 10 by screws 22. Low voltage wires 24 connect motor 7 to RCA jack 25 at motor solder tabs 8. Frame 10 includes opening 10A and lock screws 11 which secure motor 7 in frame 10 and allow for rapid and easy replacement of motor 7 if necessary. In the preferred embodiment, the opening is circular, however, it is understood that any opening necessary to accomodate any dimension motor could be utilized. Motor 7 allows for variable rotational motion of motor shaft 6 over a speed range of approximately 3000 to 8500 RPMs. Motor shaft 6 engages a drive mechanism which comprises a counter balance flywheel 5 which includes a cam pin 3, a lock clip 4, bearings 1A through 1C, cam 2, and a needle cone 9. Needle 26 hook end 26A loops over and engages needle cone 9 and linearly reciprocates therewith. Motor shaft 6 engages the drive mechanism through an opening 5A at the base of counterbalance flywheel 5 and is secured therein. The motor shaft 6 rotational motion causes needle cone 9 to linearly reciprocate with cam 2. The cam pin 3 is offset from the central axis of counterbalance flywheel 5 and forces cam 2 to reciprocate as offset cam pin 3 follows a circular motion about, and spaced apart from the central axis of motor shaft 6. Bearings 1A and 1B insert within cam 2 and comprise an opening to receive cam pin 3 therethrough. Cam 2 is thus rotatably mounted to cam pin 3 and effectively allows for the rotational motion of cam pin 3 to translate into linear reciprocating motion of cam 2. Bearing 1C also inserts within cam 2 to secure needle cone 9 therein. Frame 10 further includes an opening 27A to receive a needle tube 27 that is secured therein by tightening knob 17. Frame 10 can accommodate varying dimensioned needle tubes 27 by varying the frame 10 clamping force on needle tube end 27B via tightening knob 17. Frame 10 includes a split end portion 10B that expands and contracts via a tightening knob 17 screwably engaging end portion 10B. The knob 17, when turned in the clockwise direction, forces split end portion 10B to clamp against needle tube end 27B. Split end portion 10B can accept various dimensioned tubes 27. Needle 26 is contained within needle tube 27 with needle hook end 26A extending through frame 10 opening 27A and onto needle cone 9. The length of extension of needle hook end 26B out of tube 27 is adjustable by varying the placement of tube 27 within opening 27A. A guide mechanism supports needle 26 at a point adjacent to needle hook end 26A. The guide mechanism comprises a needle bar plastic guide 13 with guide slot 13A for alignment of needle 26. The guide mechanism further comprises a horseshoe shaped guide frame 12 that extends through plastic guide 13, through tension springs 14, and through frame 10 openings 15. The guide frame 12 is secured within frame 10 by guide lock screw 16. Referring to FIG. 1A, the guide mechanism is tensioned by elastic 19A at location 26AB which is adjacent to needle hook end 26A. Elastic 19A extends around needle 26 and needle tube 27 providing a downward tension to needle hook end 26A and needle bar plastic guide 13, thereby securing needle 26 within slot 13A and compressing guide tension springs 14. Elastic 19A is secured to frame 10 by barbell 19 which extends through frame 10 and allows for elastic 19A to be wrapped around needle hook 26 and needle tube 27. FIG. 1B illustrates a detailed view of the placement of elastic 19A. The guide mechanism allows for the needle hook end 26A to securely loop over needle cone 9. The elastic tension keeps needle hook end 26A engaged with needle cone 9. The horseshoe guide frame 12 and plastic needle bar guide 13 maintain needle 26 reciprocating linear motion and prevent side forces generated by cam 2 from bending needle 26 or causing needle 26 to engage in non-linear motion.

It should be understood that the preceding is merely a detailed description of one embodiment of this invention and that numerous changes to the disclosed embodiment can be made in accordance with the disclosure herein without departing from the spirit or scope of the invention. Rather, the scope of the invention is to be determined only by the invention claims and their equivalents.

I claim:

1. A reciprocating shaft device for marking an article with ink, comprising:
    a frame having a first end portion, a second end portion, and a middle portion, said first end portion having a first opening, said second end portion having a second opening;
    a motor mounted within said first opening, said motor including a rotatable shaft;
    a detachable grip tube, one end of said grip tube slideably engaging said second opening, said grip tube including a reciprocal needle bar therein, said needle bar having a proximal and distal end;
    a drive means for converting rotary motion of said shaft into reciprocating motion of said needle bar, said drive means connected at one end to said shaft, said drive means further connected at the other end to said proximal end of said needle bar;
    a needle stabilization means for limiting movements of said needle to linear reciprocating motion, said needle stabilization means including a guide means for limiting side to side movement of said needle, said guide means attached to said middle portion of said frame, said proximal end of said needle bar tensioned against said guide means, said needle stabilization means further including tension means for providing a downward tension on said needle bar, said guide means of said needle stabilization means further includes a needle bar guide, said needle bar guide including a top and bottom portion, said needle bar proximal end tensioned against said needle bar guide top portion, said needle bar guide further including a guide frame slideably extending through said needle bar guide, said needle bar guide movable along said guide frame, said guide frame affixed to said middle portion of said frame, said needle bar guide further including tension springs, said tension springs biased downward by said bottom portion of said needle bar guide under force from said tensioned needle bar proximal end.

2. A reciprocating shaft device as in claim 1, wherein said drive means further includes:
    a counterbalance flywheel, said flywheel comprising a cam pin, said cam pin offset from the axis of rotation of said rotatable shaft of said motor, said cam pin extending longitudinally upward from the top of said flywheel, said flywheel further comprising a shaft hole at the base of said flywheel, said shaft hole securing said rotatable shaft therein, said flywheel further comprising a cam, said cam rotatably engaging said cam pin at one end, to allow the rotational motion of said cam pin to translate into linear reciprocating motion of said cam, said cam further including at the opposite end connection means for engagement of said proximal end of said needle bar to said drive means.

3. A reciprocating shaft device as in claim 2, wherein said connection means is cone shaped, said proximal end of said needle bar looping around said cone.

4. A reciprocating shaft device as in claim 2, wherein said one end of said cam further comprises a first bearing insert and a second bearing insert, said first bearing insert and said second bearing insert further comprising a first and second opening for receiving said cam pin therethrough.

5. A reciprocating shaft device as in claim 3, wherein said cone shaped connection means further includes a protuberance extending outward therefrom, said protuberance engaging a third bearing insert, said third bearing insert fixed between said cone shaped connection means and said opposite end of said cam.

6. A reciprocating shaft device as in claim 1, wherein said second end portion is split, said split second end portion including tightening means therethrough for contracting or expanding said second opening.

7. A reciprocating shaft device as in claim 6, wherein said tightening means is a tightening knob, said knob screwably engaging said split end portion.

8. A reciprocating shaft device as in claim 1, wherein said guide frame extends through said tension springs.

9. A reciprocating shaft device as in claim 1, wherein said tension means is an elastic.

10. A reciprocating shaft device as in claim 9, wherein said elastic has a first end, a middle end, and a second end, said first and second end attached to said frame, said middle end providing said downward tension to said needle bar.

11. A reciprocating shaft device as in claim 1, wherein said guideframe includes a horseshoe shaped end, said end extending above said top portion of said needle bar guide, said end encircling said downward biased needle bar.

12. A reciprocating shaft device as in claim 1, wherein said top portion of said needle bar guide includes a guide slot, said needle bar proximal end biased downward and secured into said guide slot by said tension means.

13. A reciprocating shaft device as in claim 1, wherein said motor mounted within said first opening is secured with locking screws, said screws allowing for the rapid and easy replacement of said motor.

14. A reciprocating shaft device as in claim 1, wherein said motor is adjustable between 3000 and 8500 revolutions per minute.

15. A reciprocating shaft device as in claim 1, wherein said middle portion and said second end portion are at a ninety degree angle.

16. A reciprocating shaft device as in claim 1, wherein said second opening of said second end portion is elevated above said first opening of said first end portion.

* * * * *